United States Patent
Sarin et al.

(10) Patent No.: US 6,711,431 B2
(45) Date of Patent: Mar. 23, 2004

(54) NON-IMAGING, COMPUTER ASSISTED NAVIGATION SYSTEM FOR HIP REPLACEMENT SURGERY

(75) Inventors: Vineet Kumar Sarin, Thousand Oaks, CA (US); Clyde Ronald Pratt, Somis, CA (US); Mark Edward Apgar, Oxnard, CA (US); William Ralph Pratt, Newbury Park, CA (US)

(73) Assignee: Kinamed, Inc., Camarillo, CA (US)

( * ) Notice: Subject to any disclaimer, the term of this patent is extended or adjusted under 35 U.S.C. 154(b) by 0 days.

(21) Appl. No.: 10/075,796

(22) Filed: Feb. 13, 2002

(65) Prior Publication Data

US 2003/0153829 A1 Aug. 14, 2003

(51) Int. Cl.$^7$ ................................................. A61B 5/05
(52) U.S. Cl. ........................ 600/426; 600/429; 606/130
(58) Field of Search ........................ 606/130; 600/424, 600/427, 429, 426

(56) References Cited

U.S. PATENT DOCUMENTS

| | | | |
|---|---|---|---|
| 5,665,090 A | | 9/1997 | Rockwood et al. |
| 5,807,252 A | | 9/1998 | Hassfeld et al. |
| 5,880,976 A | * | 3/1999 | DiGioia, III et al. ........... 703/7 |
| 6,061,644 A | | 5/2000 | Leis |
| 6,205,411 B1 | | 3/2001 | DiGioia, III et al. |
| 6,430,434 B1 | | 8/2002 | Mittelstadt |
| 2002/0077540 A1 | * | 6/2002 | Kienzle, III ................ 600/424 |

OTHER PUBLICATIONS

George E. Lewinnek, et al., "Dislocations after Total Hip–Replacement Arthroplasties," Journal of Bone and Joint Surgery, vol. 60–A, No. 2, Mar., 1978, pp. 217–220.

Anthony M. Digioia, et al., "Image Guided Navigation System to Measure Intraoperatively Acetabular Implant Alignment," in Clinical Ortho–paedics and Related Research, No. 355, pp. 8–22, 1998 (Lippincott Williams and Wilkins, publishers).

Branislav Jaramaz, Anthony M. Digioia, et al. "Computer Assisted Measurement of Cup Placement in total Hip Replacemnet," in Clinical Orthopaedics and Related Research, No. 354, pp.70–81, 1998 (Lippincott Williams and WilkIns, publishers).

* cited by examiner

Primary Examiner—Michael J. Milano
Assistant Examiner—D. Jacob Davis
(74) Attorney, Agent, or Firm—William L. Johnson

(57) ABSTRACT

The invention includes: a locating system; a computer, interfaced to the locating system and interpreting the positions of tracked objects in a generic computer model of a patient's hip geometry; a software module, executable on the computer, which defines the patient's pelvic plane without reference to previously obtained radiological data, by locating at least three pelvic landmarks; and a pelvic tracking marker, fixable to the pelvic bone and trackable by the locating system, to track in real time the orientation of the defined pelvic plane. Preferably, the system also includes a femoral tracking marker, securely attachable to a femur of the patient by a non-penetrating ligature and trackable by the locating system to detect changes in leg length and femoral offset.

5 Claims, 6 Drawing Sheets

IMPACTOR POSITION

SHELL POSITION

LINER POSITION

HEAD CENTER CHANGE

LEG LENGTH CHANGE

HEAD OFFSET CHANGE

NOTE: RIGHT PEDAL SEND SUMMARY TO PRINTER, ALONG WITH PATIENT DATA. SAVE ALL DATA TO FILE SPECIFIC TO THIS RUN OF SOFTWARE. CHANGE SECURITY FLAG SO THAT SAME CD CAN NOT BE USED TO START PROGRAM AGAIN.

NON-IMAGING, COMPUTER ASSISTED NAVIGATION SYSTEM FOR HIP REPLACEMENT SURGERY

BACKGROUND OF THE INVENTION

1. Field of the Invention

This invention relates to computer assisted surgery generally and more specifically to computer assisted total hip replacement (THR) or hip arthroplasty operations.

2. Description of the Related Art

Total hip replacement or arthroplasty operations have become increasingly common in the United States, with more than 300,000 such operations occurring annually. Many of the procedures will eventually require revision, due to one of any number of problems. Problems can arise with the implant, which can wear, degrade or even fracture. In other cases, dislocation of the replaced hip can occur, causing extreme pain (not to mention inconvenience and expense). The incidence of dislocation has remained at approximately 2–6 per cent, in spite of improvements to technique and materials.

It is known that the incidence of post-surgical dislocation is related to the orientation of the hip replacement components, particularly to the angular orientation of the acetabular shell component in relation to the bony anatomy. See Lewinnek et al., "Dislocation after total hip-replacement Arthroplasties," *Journal of Bone and Joint Surgery*, Vol. 60A, No. 2, PP. 217–220 (1978). The head and neck geometry of the implant is also thought to be a factor.

In spite of the published research, the typical surgeon has not adopted any sophisticated method of navigating hip replacement surgery, in spite of the availability of several techniques. The most prevalent method is to rely on an acetabular impactor tool with a handle placed at an angle predetermined so that if the handle is maintained at a level, horizontal orientation, the acetabular shell will be at a desired angle. This method fails to consider the considerable movement and variation in the patient's pelvic position during surgery; at worst it aligns the shell with the operating table (not necessarily the pelvis). More technological methods have been developed, including the sophisticated method described in U.S. Pat. No. 6,205,411 (and related applications) to DiGioia et al. (2001). The method of DiGioia is an advance over the prior methods (which he summarizes authoritatively in his "Background" section).

DiGioia's method begins with extensive pre-operative imaging, including relatively expensive CT scanning. The pre-operative imagery is then input into a digital computer model, which performs extensive, three-dimensional modeling including range of motion simulations of the patient's anatomy in relation to a specific computer model of a particular implant,. Next, in an intra-operative phase, the pre-operative models are registered with intra-operative optical tracking data: a very large number of points are sampled on the pelvis and femur, and the computer fits the data to the pre-operative model. Finally, the implant is positioned to align as closely as possible with the optimized computer model.

The method of DiGioia et al. is complex and requires sophisticated digital and radiological techniques. A need still exists for a simpler method of surgical navigation which will facilitate proper hip geometry with a minimum of pre-operative imagery and expense. It is frequently found that physicians are loath to adopt any methods, and particularly any computerized methods, which are unduly complex, expensive or time consuming. In this they may be forgiven, in light of the increasing economic constraints which burden the modern practice of medicine.

Thus, a need persists for an intra-operative computer assisted hip navigation system which is easily learned, rapidly executed, economically practical, and independent from expensive or exotic pre-operative radiological imagery.

SUMMARY OF THE INVENTION

In view of the above problems, the present invention includes a method and system for intra-operative navigation of a hip replacement operation which permits a surgeon to intra-operatively assess the orientation of an acetabular shell implant and/or the orientation of a femoral stem implant, without recourse to pre-operative imagery or computerized simulations.

According to one aspect, the invention is a computer assisted, non-radiological method of intra-operatively measuring and assessing relative geometric relationships among skeletal features of a hip joint, suitable for surgical navigation of a hip arthroplasty operation. The method includes the steps: defining a pelvic plane from at least three recognizable anatomic features of the pelvis; tracking with an optical tracking system the orientation of an acetabular implant, to obtain acetabular implant orientation data; and adjusting the acetabular implant into a desired orientation with respect to the defined pelvic plane, without reference to previously obtained radiological data, by relating the acetabular implant orientation data to the defined pelvic plane.

According to another aspect, the invention includes a device for tracking the upper femur, suitable for use during a hip arthroplasty operation. The device includes: a rigid collar which can engage the greater trochanter; an optical tracking target, mounted on the rigid collar; and a ligature, attached to the rigid collar and capable of being wrapped around the upper femur and tensioned to urge the collar against the greater trochanter, for attaching the rigid collar to the femur.

Still another aspect of the invention is a method of attaching a tracking marker to the upper femur, suitable for tracking the upper femur during hip arthroplasty or a similar operation, including the steps: positioning a rigid collar in contact with the greater trochanter of the femur, the collar adapted for mounting thereon a tracking marker; attaching a ligature or opposable clamp to the collar; wrapping the ligature around the upper femur; and tightening the ligature or clamp around the femur to pull the collar tightly against the greater trochanter.

Another aspect of the invention is a method of determining changes between (1) pre-operative femoral position and (2) post-operative implant geometry, suitable for use during a hip arthroplasty operation, including the steps of: Maneuvering the femur into a reference position; measuring, with a non-radiological optical tracking device, pre-replacement femoral parameters; after implanting a prosthetic, returning the femur to the reference position; again measuring, with a non-radiological optical tracking device, post-replacement femoral parameters; and comparing the pre-replacement and the post-replacement parameters in a computer model.

The system of the invention includes: a locating system; a computer, interfaced to the locating system and interpreting the positions of tracked objects in a generic computer model of a patient's hip geometry; a software module, executable on the computer, which defines the patient's pelvic plane without reference to previously obtained radiological data, by locating at least three pelvic landmarks; and a pelvic tracking marker, fixable to the pelvic bone and trackable by the locating system, to track in real time the orientation of the defined pelvic plane.

Preferably, the system also includes a femoral tracking marker, securely attachable to a femur of the patient by a non-penetrating ligature and trackable by the locating system to detect changes in leg length and femoral offset.

Preferably, a system in accordance with the invention also includes a method of verifying reliability of a computer assisted, optically tracked surgical navigation system. According to this method, a fixed optical tracking marker is tracked in relation to a fixed reference mark on the same bone, both before and after the surgical procedure. This provides a check ("tracker check") to detect any errors due to, for example, slippage, drift, or deformation of the apparatus.

These and other features and advantages of the invention will be apparent to those skilled in the art from the following detailed description of preferred embodiments, taken together with the accompanying drawings, in which:

DETAILED DESCRIPTION OF THE INVENTION

Figure 1:
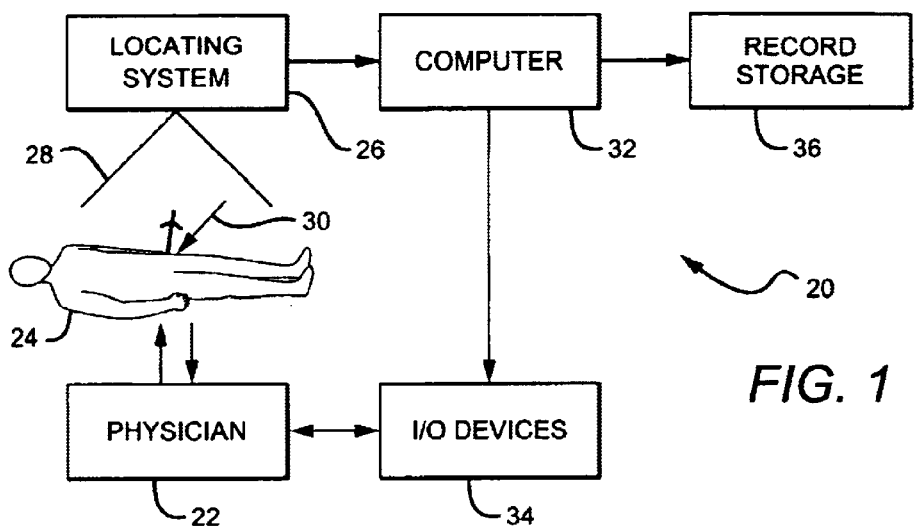
FIG. 1 is a system-level block diagram of the apparatus of the invention in a typical surgical environment.

FIG. 1 shows a system-level block diagram of the system or apparatus 20 of the invention in a typical operating room environment. A physician or other professional 22 performs a hip surgery (for example, total hip replacement) on a patient 24. An optical or equivalent locator or locating system 26 is disposed near the patient, so that the operating field is encompassed substantially within the field of view 28 of the locator 26. A suitable optical locator is available commercially, for example the "Polaris" available from Northern digital Inc., in Waterloo, Ontario, Canada. Optical trackers or markers 30 are used during the operation, as more fully described below in connection with FIGS. 3–7. The markers 30 allow the locator 26 to acquire the positions and orientations of tools and anatomical reference points, as described below.

The optical locator 26 is interfaced with and outputs tracking data to a digital computer 32, which interprets the optical tracking data as it is received. Using well known geometric relationships, the computer is programmed to deduce from the optical field of view the actual positions and orientations of the markers, and, by extension, the positions and orientations of the instruments and/or anatomical features that are in known relationship to the markers. For example, suitable optical markers utilizing multiple reflective spheres are available from Traxal, Inc. in Toronto, Ontario, Canada. Markers with active light emitting devices such as LEDs are also available and could equivalently be used. Note that typical markers include three or more non-collinear components; this allows the locator and computer to determine not only the positions but the orientation (rotation) of such a marker in space. This capability is exploited in the methods described below.

Preferably, the computer 32 is also programmed with a user-friendly interface (software) which facilitates the execution of the method of the invention (described below in connection with FIG. 2). The physician or other personnel can view output (for example on a video monitor) and input instructions to the computer 32 via I/O devices 34, which suitably could include a monitor, keyboard, printer, foot pedals, and other input/output devices such as conventional "mouse" or similar pointing devices.

Preferably, the system also includes a record storage device 36 such as a CD-R drive, and/or simply a printer which prints out a summary of the operation and patient data for future reference or medical archiving.

Figure 2:
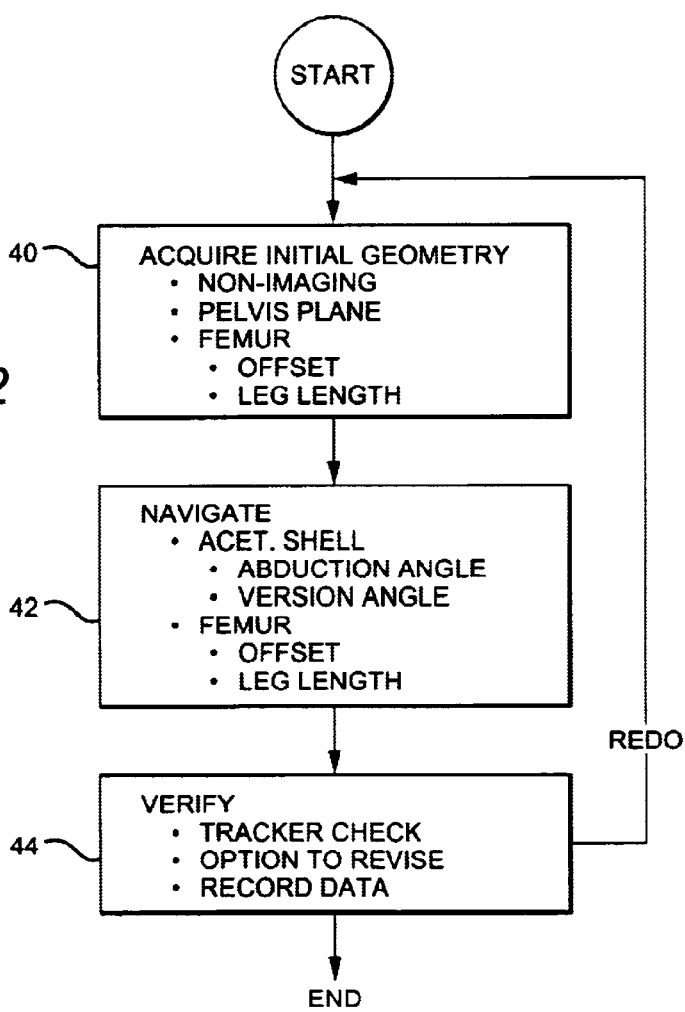
FIG. 2 is a high-level flow diagram of the method of the invention.

FIG. 2 is a top-level flow diagram of the method of the invention, showing the steps of the method at a high level of abstraction. Specific steps are elaborated and explicated in connection with later figures, along which particular surgical apparatus suitable for practicing the method.

In broad terms, the method includes three major steps, all performed intra-operatively: Acquisition of patient geometry (40), computer aided navigation of surgery (42), and computer aided verification (44) of implant geometry.

Patient geometry is acquired (in step 40) by attaching and optically tracking several optically trackable markers, described below in connection with FIGS. 3–5. Note that the acquisition of patient geometry according to this method does not utilize any radiographic or other imaging.

After acquiring the initial or "native" geometry of the patient's pelvic-femoral system, in step 42 the method uses continuous or near-continuous, real-time optical tracking of the pelvis and femur as well as surgical tools, including an optically trackable impactor or equivalent tool for positioning and fixing an acetabular shell implant. Computer acquired and calculated information is displayed to the surgeon in real time to facilitate placement of the acetabular shell implant within a desired angular range of anteversion and abduction (and preferably also a desired range of anterior/posterior angulation or "flexion") The femur is also tracked and computer graphic display allows the surgeon to achieve a desired amount of femoral offset and a desired leg length (typically very nearly matching the native length and offset on the opposite side of the body).

Finally, in step 44 the orientation and position of pelvic and femoral tracking markers are preferably verified by optical tracking and computer calculation, by a method of redundant checking ("tracker check"). This step reveals any inconsistencies, such as might occur due to slippage or bending of instruments, or other errors. If any significant discrepancy is revealed during verification, the surgeon has the option to repeat some or all of the surgical procedure before terminating the procedure.

Preferably, the verification step 44 also includes making and storing permanent records of the procedure, including patient and implant geometry, for archiving or medical reference. The record can be in machine readable, and/or human readable form. For example, a printout is preferably generated which can be entered into a traditional medical filing system, together with a machine-readable record of the operation, for example on CD-R.

The more detailed procedural explanation given below in FIGS. 8 through 13 makes frequent reference to certain optically trackable markers and tools which are specifically adapted for the invention. Visualization of the procedure thus will be greatly facilitated by first considering typical trackable markers and tools.

Figure 3:
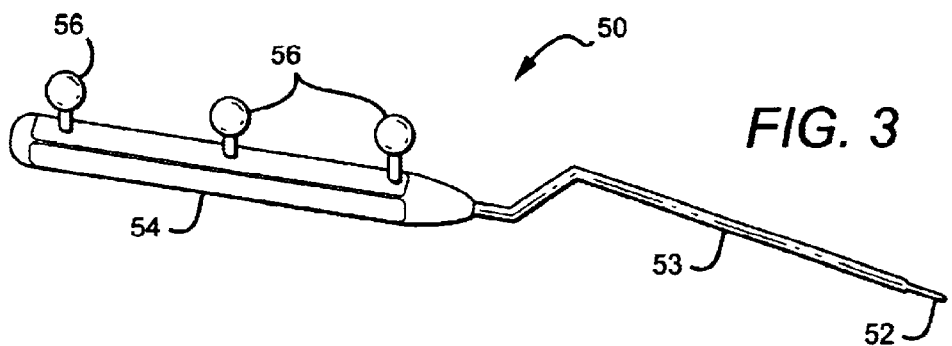
FIG. 3 is a perspective view of an optically trackable manual probe suitable for use to input positional information in the method of the invention.

A typical optically trackable manual probe 50 is shown in FIG. 3. This probe includes a pointable tip 52 at the front end of an elongated stem 53 of known length and shape. The rearward end of the stem 53 is fixed to a rigid body 54 of known dimensions and geometry, suitably shaped for hand-gripping. Mounted to the body 54 is an optical tracking target 56 having at least three optical tracking references. Both active and passive references, targets, and probes are available commercially, for example from Traxal, Inc. in Toronto, Ontario, Canada.

It is known that an optical tracking target such as 56, with known dimensions and geometry, can be optically tracked for example by an optical locating system available from Northern Digital, Inc. (referenced previously). Since the dimensions and shape of the stem 53 and body 54 are known, tracking of the position and orientation of target 56 allows ready calculation of the position of the tip 52 by well known geometric relationships. Thus, to enter a spatial location (such as an anatomical landmark) into to computer 32, a physician can touch the tip 52 to the location while simultaneous cueing the computer to input the instant position. A foot switch is a typical and convenient method of cueing the input.

Figure 4:
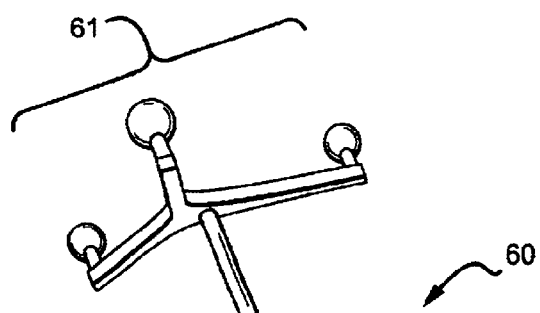
FIG. 4 is a perspective view of another optically trackable position marker suitable for fixation to the pelvis for tracking the position and orientation of the pelvis.

FIG. 4 shows a similar optically trackable pelvic marker shown generally at 60, which includes a trackable marker 61 adapted for fixation on a bone screw 62, and suitable for intra-surgical fixation to any convenient exposed surface of the pelvis. Note that a quick release device 64 is preferably provided between the target 56 and the bone screw 62. The quick release device 64 allows the trackable marker 61 to be quickly attached or detached as required during surgery. Detachment of the marker 61 is convenient for the surgeon, lest he find his movements encumbered by its presence. The quick-release device should be designed to provide well defined, stable, and reproducible positioning of the marker 61 with respect to the bone screw 62.

Figure 5:
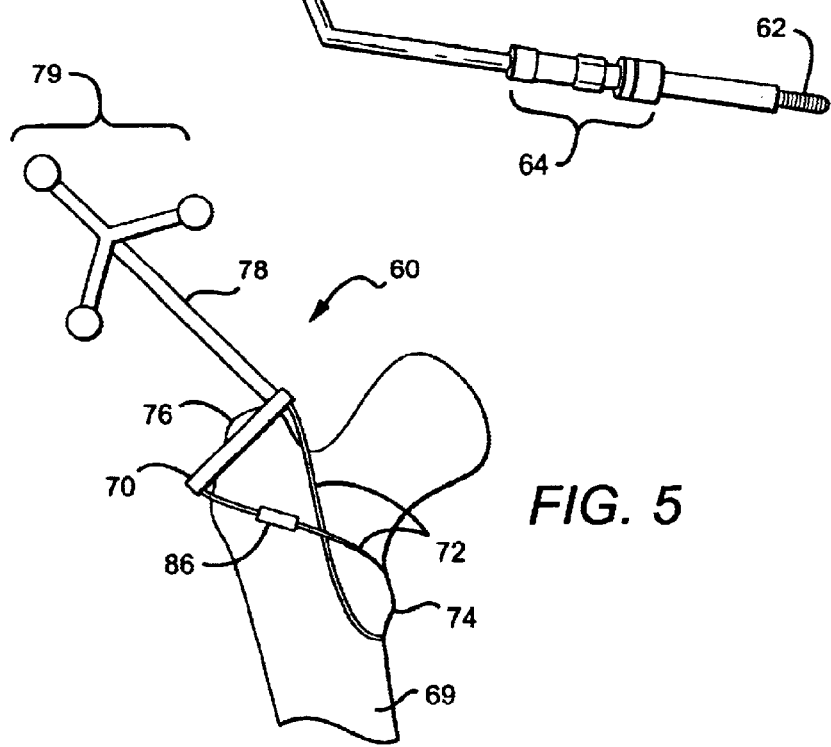
FIG. 5 is a perspective view of yet another optically trackable marker adapted for fixation to the femur to track position and orientation of the femur.

FIG. 5 shows generally at 68 a femoral tracking marker device fixed in a typical manner on a patient's femur 69 near the greater trochanter. It is extremely preferable that this device be fixable to the femur in a firm and fully engaged position which does not allow slippage or rotation, but without the use of bone screws, pins or any other bone damaging devices. Specifically, it is extremely preferable that the marker 68 is attachable to the femur by a device which does not penetrate the outer cortical (hard) shell of the bone. It is permissible, in accordance with the invention, to use aggressively textured surfaces, which could include spikes or cleats which do not penetrate the outer cortical shell.

Accordingly, the preferred embodiment shown employs an ellipsoidal indexing collar 70 and elongated tensioning members 72 which wrap around the femur 69. One advantageous position of the tensioning members 72 is shown, with independent tensioning members running above and below the projection of the lesser trochanter 74 to secure the placement from axial slippage. The tensioning members 72 pull the indexing collar onto the projection of the greater trochanter 76. Because of the irregular shape of the greater trochanter 76, we have found that the ellipsoidal indexing collar 70 tends to seek a stable position vis-à-vis the greater trochanter 76, which position is maintained firmly by the tensioning members 72.

A shaft 78 is fixed to the indexing collar 70 at a first end and supports at a second end an optical tracking target 79, similar to those previously described. The shaft 78 may optionally have a bend, articulation, or joint (not shown, to maintain clarity of the drawing) to allow the marker to be oriented in a better aspect for optical tracking.

The tensioning members 72 collectively comprise a "ligature". It should be understood that the term "ligature" is used in its most general sense: as something which binds, unites or connects. The tensioning members 72 are suitably made from elastomeric fibers or cords such as those available from Poly 4 Medical in Goleta, Calif. Other materials or other flexible members such as wire, bands, mesh, spring, cords, ligaments or string could alternatively be used in a wrapping arrangement to comprise the ligature. It is desirable that the tensioning members 72 be so constructed that they are capable of exerting sufficient force to firmly attach the marker device, but are not so strong that a crushing force could be accidentally exerted on the femur. To attach a typical marker device 68, the surgeon threads the tensioning members 72 through a slot (82 in FIG. 6, below), encircles the femur, and threads through an opposing slot (84 in FIG. 6, below). He then pulls the tensioning members to an appropriate tension and attaches a clamp 86 to hold the member in tension. Suitable clamps are available from Poly 4 Medical, but other means of holding the members in tension could be used, such as various hooks or staples.

Figure 6:
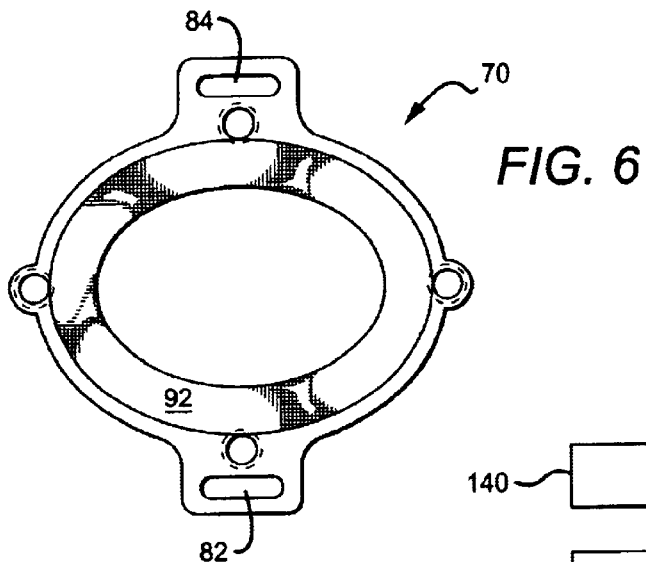
FIG. 6 is a plan view of the indexing collar, also shown in FIG. 5, which facilitates secure attachment of the tracking marker to the patient's femur without penetrating devices or screws.

FIG. 6 shows a typical collar 70 in isolation. The aperture 90 of the collar is preferably elliptical, with major axis a and minor axis b in the range of 30 mm to 45 mm (major axis) and 20 mm to 35 mm(minor axis). Other shapes could be used, including ellipsoidal, horseshoe, "U" or irregular shapes. A range of collars of varying sizes may be advantageously kept available for the surgeon to accommodate various patients. The collar preferably has an inward facing bevel 92 at approximately a 45 degree angle, defining an angled shoulder which is preferably knurled or otherwise textured to grip the trochanter in a positive manner.

The femoral tracking marker 68 of the invention is extremely advantageous and is preferred over prior devices such as bone screw tracking devices (such as that described in U.S. Pat. No. 5,807,252 to Hassfeld et al.). Such bone screw devices are commonly used in knee replacement surgery. The upper femur, however, is less amenable to bone screw attachment. Because of the mechanics of the hip and upper femur, the upper femur experiences very large stress and shearing forces, both in its natural state and after implantation of an artificial hip prosthesis. In extreme cases this stress can actually cause the prosthetic stem to fracture the upper femur. Thus, it is desirable to avoid placement of any penetrating device such as a bone screw into the upper femur, as the penetration could compromise the structural integrity of the bone tissue. The femoral tracking device of the invention thus permits convenient and quick attachment without fully penetrating the outer cortical (hard) shell of the femur.

Alternatively, a clamp, fixable to the femur and/or the greater trochanter, could be used to attach the tracking marker to the femur; but the collar and ligature described above is preferred, as it provides a convenient and secure attachment. Whatever method is used, it is extremely preferable to avoid fully penetrating the outer cortical (hard) shell of the femur.

Figures 7, 14:
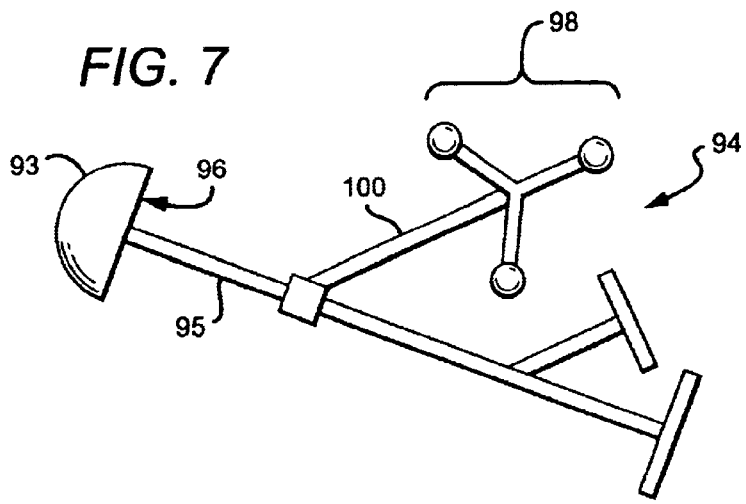
FIG. 7 is a perspective view of an acetabular component placement tool ("impactor"), equipped with a tracking marker in accordance with the invention.
FIG. 14 is a typical printout/record produced by the method of the invention for archiving and/or retention in the patient's medical records.

One further trackable tool is useful. FIG. 7 shows the acetabular shell component 93 mounted on the impactor placement tool 94. Typically the shell component 93 is essentially a sliced spherical shell, which may be hemispherical or describe less than half of a sphere. The impactor tool 94 preferably has a shaft 95 which is fixable to the shell 93, for example by a pressed fit or threaded mating device. Once fixed, the shaft is held at a known orientation with respect to the shell. It is particularly convenient if the shaft 95 is fixed normal to the plane of the lip 96, as shown in the figure. An optically trackable marker 98 is mounted to the impactor shaft 95, but offset by a secondary shaft 100 (which may optionally include a quick release device). The marker 98 is held in fixed angular relation to the impactor shaft 95, so that by locating the orientation of marker 98, the angle of the shaft 95 is easily also determined. This tool is employed during the "navigation" step of the method (described below). The preceding discussion of the preferred optical tracking markers should be borne in mind while considering the following detailed procedural descriptions of the preferred method of the invention.

Figure 8:
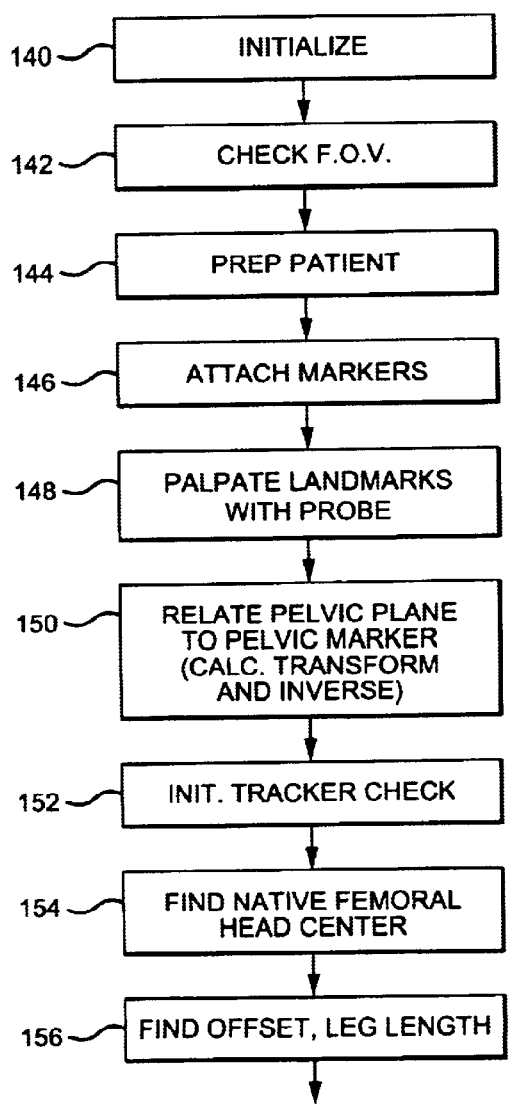
FIG. 8 is a flow diagram of detailed steps suitable for executing the acquisition step of FIG. 2.

FIG. 8 shows in greater detail preferred steps which are included in the acquisition step (40 in FIG. 2). Preliminary steps 140–144 are conventional. In step 140, the system is initialized: a welcome screen appears and the physician or other professional enters relevant patient and physician information. Next (step 142) the physician checks the field of view with an optically trackable pointer such as that described above in connection with FIG. 3. The surgical field should be arranged to lie substantially within the field of view 28 of the optical tracker 26 (in FIG. 1) yet close enough to the optical tracker to allow a high degree of tracking accuracy. Next the patient is prepared for surgery in a conventional manner and introduced into the field of view (step 144).

Note that no pre-operative computer modeling or high-resolution radiological imaging (such as a CAT scan) are included in the method of the invention (although a physician typically will have consulted previous X-ray images before surgery)

Next, in step 146, the physician attaches at least one pelvic marker 60 and at least one femoral tracking device 68 (discussed above in connection with FIGS. 4 and 5). The pelvic tracking marker 60 is suitably attached by inserting a bone screw or other fixing device into an exposed portion of the pelvic bone. In contrast, according to the invention the femoral tracking marker 68 is attached without penetrating bone screws, as described previously. By avoiding insertion of bone screws into the femur, the invention prevents injury or mechanical compromise of the highly stressed upper femur, thereby lessening the likelihood of post-operative complications due to femoral fracture.

Next, in pelvic definition step 148, the physician uses an optically trackable manual probe 50 to palpate at least three, and preferably four, easily located anatomical landmarks on the pelvis. This is accomplished, for each landmark, by activating a foot pedal or other switch while simultaneously positioning the probe in percutaneous contact overlying a prominent anatomical landmark. When thus cued, the computer 32 receives apparent positional information regarding the probe from the optical tracking system 26 and calculates from this information a position for the corresponding landmark in a reference frame attached to the pelvic marker 60.

The reference landmarks in the pelvic definition step 148 are suitably chosen from: the ipsilateral anterior superior iliac spine (ipsilateral "ASIS"), a contralateral anterior superior iliac spine (contralateral "ASIS"), an ipsilateral pubic tubercle, and a contralateral pubic tubercle. Basic geometry dictates that at least three points are required to define a plane. However, preferably all four of the above mentioned reference landmarks should be input into the computer system to better define a pelvic plane. One suitable method is to define an imaginary point at the midpoint of the line segment between the two pubic tubercles. This midpoint is then used, together with the two ASIS, to define the pelvic plane. Suitably, the computer can choose a plane by a least squares minimum error fit to the four points, if any asymmetry exists. A Pelvic Coordinate frame of reference is also defined in this step, suitably with origin at the midpoint between the ASIS. a suitable coordinate frame is more fully described below in connection with FIGS. 9 and 10.

Note that the pelvic reference plane ("anterior pelvic plane") is an imaginary plane defined by 3 points; no effort is made to curve fit to a complete, non-planar model of the pelvic bone. Indeed, no such model is assumed to be available, as no pre-operative CT or MRI scan is required by the method.

Next, in step 150, the computer relates the pelvic reference plane (calculated from step 148) to the reference frame of the pelvic tracking marker. That is to say that the pelvic tracking marker, firmly attached to the pelvic bone at some hitherto unknown orientation, defines a pelvic tracking marker reference frame (PTMRF, an orientation and position of the marker). The pelvic coordinate system that was calculated in step 148 is related to the PTMRF by a rotation and translation, and this relationship is calculated and stored. Differently stated: The pelvic reference frame found by palpating landmarks defines a first coordinate system; the position and orientation of the fixed pelvic tracking marker defines a second coordinate system, related to the first by an affine transformation. The affine transformation (and preferably the inverse transformation) are calculated by well known means and stored.

Next, in optional step 152, a redundant accuracy check ("Tracker check") is initialized. Preferably, a redundant reference mark is placed on the pelvis at some position other than that of the fixed pelvic tracking marker. Cauterization is a suitable and convenient method of marking the pelvis, but other methods could also be used. The physician then touches the redundant reference mark with an optical tracking probe, while cueing the computer (for example by foot switch) to input the tracker's position. The computer then calculates the position of the redundant reference mark in relation to the pelvic tracking marker reference frame (PTMRF). The vector thus defined is stored for future reference (during navigation steps, described below).

Next, (step 154) the physician (in coordination with the program execution of computer 32) pivots the femur, typically in arcs or circles consistent with its natural arcs of movement. The movements of the femoral tracking marker are tracked by the optical locating system 26 and interpreted by the computer 32 to calculate the natural or "native" femoral head center (referred to as "C1"). This is suitably accomplished by assuming that the motion of a point on the femur is constrained to lie on a partial spherical surface with its center at the native head center. A least squares surface fitting algorithm is suitably used to calculate the center of the sphere (C1).

After finding the native head center, the physician disposes the femur in a natural reference position ("Position 1"), preferably aligned with the patient's spinal axis, while cueing the computer to initialize offset and leg length (step 156) by storing the tracker position for future comparison. Specifically, the position of the femoral tracking marker 68 is located by optical locating system 26 and the data is interpreted by the computer 32. The position of the femoral tracking 20 marker 68 essentially defines a position on the femur; this position is related to the pelvic tracking marker and hence the PTMRF by some relative offset and length ("leg length") which are calculated and stored for future comparison (in navigation steps, described below). Note that the offset and leg length calculated provide an arbitrary reference for relative comparison. The measurements are not absolute, and are useful only so long as the femoral tracking marker 68 remains fixed with respect to the femur and the pelvic tracking marker remains fixed in relation to the pelvis. Nevertheless, the relative position information suffices to permit meaningful comparison of the pre-operative with the post-operative leg length and offset.

These steps complete the initial acquisition of geometry (step 40 of FIG. 1).

Figure 9:
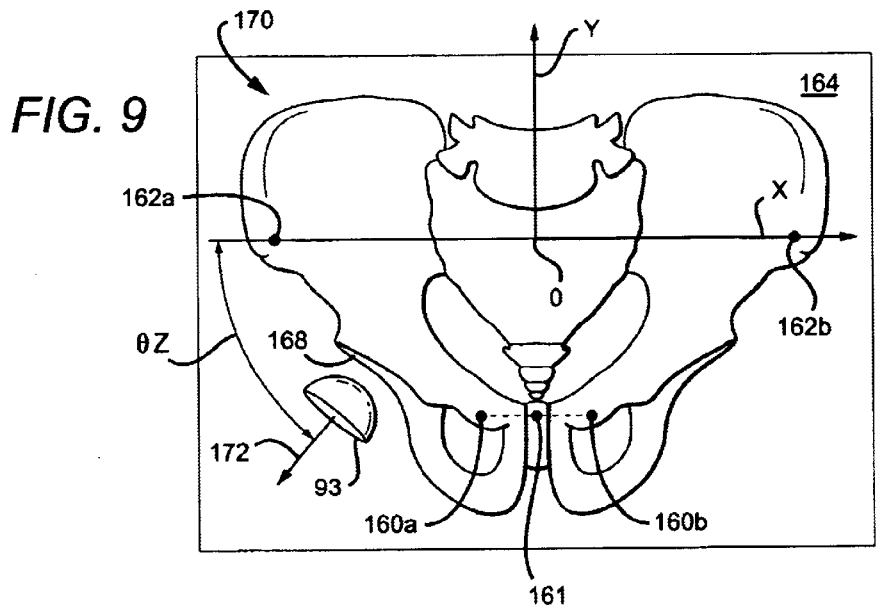
FIG. 9 is a frontal view of a pelvis, defining the pelvic plane, a pelvic coordinate system, and an abduction angle.
Figure 10:
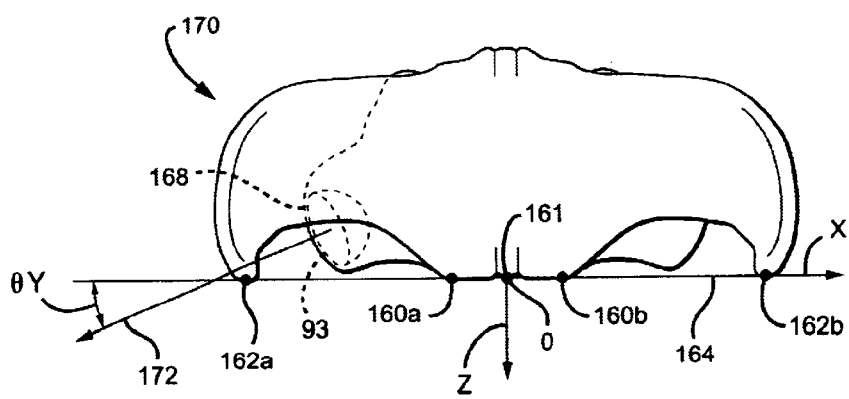
FIG. 10 is a top view of the pelvis of FIG. 9, defining a version angle.

FIGS. 9 and 10 show the pelvis and define the pelvic plane and pelvic coordinate system which references the angle of the acetabular shell implant. Right and left pubic tubercles 160a and 160b are shown, as well as the midpoint 161, in relation to right and left anterior superior iliac spines (right 162a and left 162b). All four typically lie on or near the pelvic plane 164; we define the plane by the three points: Right and left ASIS 162a and 162b and the midpoint 161 between the pubic tubercles. We define an origin O on the pelvic plane and located halfway between the right and left ASIS 162a and 162b. From the origin and pelvic plane we define right-handed, orthogonal Cartesian coordinates as shown, such that the XY plane is the pelvic plane and a Z axis is normal to the pelvic plane intersecting at origin O. An acetabular opening 168 is shown in pelvis 170. We can define the significant angles of the acetabular shell component, relative to our pelvic coordinate system. We define the axis 172 of the shell component as a vector normal to the plane defined by the rim of the component. The vector 172 intersects the plane at the center of the circle of described by the rim. With the axis 172 thus defined, we can define its orientation by θz (abduction), θy (version) and θx (anterior/posterior flexion). θz defines rotation about the z axis; it is shown as the angle of the projection of the vector 172 into the XY plane. Similarly, θy defines rotation about the Y axis; it is shown as the angle of the projection of 172 into the XZ plane. The abduction angle θz is conventionally measured from the negative Y axis; the version angle, from the negative X axis (for a right leg as shown) or the X axis (for a left leg). The third angle ("flexion", not shown) similarly defines rotation about the X axis, and is conventionally measured from the negative y axis. Flexion angle should preferably should also be measured and displayed in the method of the invention.

Note that these coordinates are equivalent to the "Anatomical" reference frame defined by and Jaramaz et al. in "Computer Assisted Measurement of Cup Placement in Total Hip Replacement," in *Clinical Orthopaedics and Related Research*, No. 354, pp. 71–81 (1998, Lippincott, Williams and Wilkins) (their FIG. 2). We have used the normal vector 172 in place of the cup plane used by Jaramaz, for ease of visualization; but both define the orientation of the cup in an equivalent way. Note that other reference frames such as the "Radiographic definition" and the "Operative definition" are also frequently used in the literature. A definition in the Anatomic reference frame can be converted to either the Radiographic or Operative reference frame by mathematical transformation (preferably performed by computer 32). Please refer to the Jaramaz article, op. cit., for more details on the various frames of reference.

Figure 11:
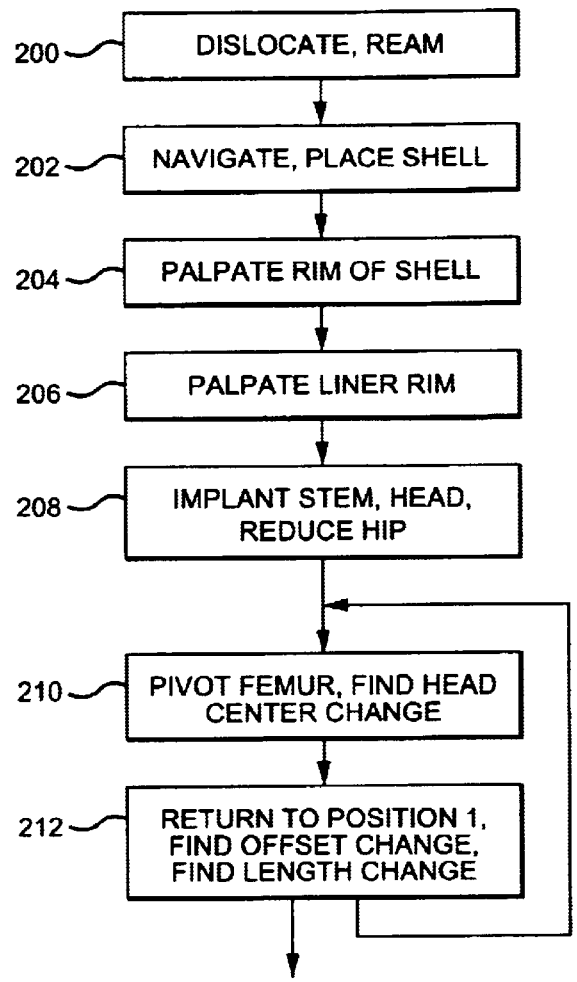
FIG. 11 is a flow diagram showing detailed steps suitable for executing the navigation step of FIG. 2.

FIG. 11 shows detailed steps of the surgical navigation step of the method (step 42 of FIG. 2, above). References to version and abduction can be easily visualized by reference back to FIGS. 9 and 10 above.

With reference to FIG. 11 next (in conventional surgical step 200) the physician will dislocate the hip and ream the acetabulum to prepare for location of an acetabular implant component ("shell"). These techniques are well known in the surgical arts and are not described here.

Once the acetabulum is prepared for the implant, the physician uses an optically trackable impactor tool 94 (described previously in connection with FIG. 7) along with the tracking system, to navigate placement of the acetabular implant shell. Specifically, the trackable impactor tool is fixed to the implantable cup. The surgeon moves the tool through a series of angles. The tool is tracked by the optical tracking system and the angles displayed via the computer 32 on the display device 34, thus providing feedback as to the abduction angle, version angle and flexion angle of the implant cup relative to the anterior pelvic plane. When the computer indicates that the desired angles have been attained, the surgeon uses impact to firmly place the acetabular cup component. A specific angle is not mandated by the invention, but rather the choice of the angle is left to the physician. Fixing screws of various types can also be used to fix the shell, as is known in the medical arts.

In the navigation step 202 the optical tracker 26 allows the computer 32 to calculate an orientation of the long axis 95 of the impactor shaft, which is fixed in known relation to the acetabular shell component. This orientation is then compared with the real-time orientation of the pelvic reference plane, as determined in real time by tracking the fixed pelvic marker (implanted in step 146 above) and thereafter applying the inverse transformation (previously determined from step 150 above). The physician manipulates the tool to align with a desired abduction angle and version angle (determined as discussed below in connection with FIG. 9). Note that the method does not require the patient to remain immobile between defining the pelvic plane (step 148) and navigation (step 202), because any motion of the pelvis is tracked by the fixed pelvic tracking marker 60. Thus, in the computer graphic model the computer moves the pelvic reference plane in concert with any pelvic displacement or rotation, in real time.

To properly align the shell, the physician moves the impactor tentatively while observing the display (34 in FIG. 1) for feedback. The optical tracking system 26 and computer 32 track in real time the orientation of the impactor tool 212 and display the orientation, along with some target or reference pattern (for example, a cross-hairs target or two protractor displays, one for version and the other for abduction angle). It has been found that 45 degrees of abduction ($\theta z$) and 20 degrees of version ($\theta y$) will typically yield an acceptable result (minimize the number of post-surgical dislocations). A range of 40 degrees +/−10 (abduction) and 15 degrees +/−10 (version) is acceptable, measured in the radiographic frame. The precise angle and range is entrusted to the discretion of the physician, based on his experience and available literature. See DiGioia et al., "Image Guided Navigation System to Measure Intraoperatively Acetabular Implant Alignment," *Clinical Orthopaedics and Related Research,* No. 355, pp 8–22 (1998 Lippincott, Williams and Wilkins); Lewinnek, et al., "Dislocations after Total Hip Replacement Arthroplasties," *Journal of Bone and Joint Surgery,* Vol 60A, No. 2, (March 1978). Once the proper orientation has been established, the shell component is set by impaction and/or screws, according to the implant system.

The orientation of the implant shell 93 is preferably next verified (step 204) by touching at least three points on the rim of the acetabular implant shell 93 with the tip 52 of probe 50 and inputting the three positions via the locating system 26. The three or more points are used by the computer to define the plane of the shell opening, which is normal to a vector 172. The orientation angles of the vector 172 (or equivalently, that of the plane of the shell opening) is then displayed to the physician and preferably recorded for future reference. Preferably, all of angles $\theta x$, $\theta y$ and $\theta z$ are displayed and recorded.

Typically a polyethylene liner is then fixed to the shell, as is known in the orthopaedic arts. Before fixing the liner, however, the liner position can be adjusted. Today's modular liners typically allow for independent adjustment of the position and orientation of the modular liner within the shell. Preferably, in step 206 the physician can capture the contour of the liner by touching at least three (and preferably more) points on the shell rim with the trackable manual probe. The optical locator and computer capture contour of the liner and preferably calculate the opening angle, orientation, of the liner, as well as the contour of the liner rim or lip. Typical liners are not hemispherical, but may have a complex shape including, for example, an extended lip or a complex chamfer. The calculated angles are then displayed to the user. The liner is then typically fixed in the shell. A still further check of proper liner placement can be optionally performed by again touching at least three points on the liner rim (step 206) to verify the position after fixation.

These steps complete the placement of the acetabular shell component (and liner). Next, the physician proceeds with the femoral component (stem and head) of the hip replacement.

Next the physician will implant (step 208) a trial femoral stem and head by conventional surgical methods not described here, and the hip is reduced. An illustrative surgery with narration is published by Kinamed, Inc. under the title "Total Hip Arthroplasty." The physician then pivots the femur (step 210) about a series of mechanically natural arcs while the computer and optical tracking system track the femoral tracking marker (in relation to the pelvic tracking marker). The set of points thus acquired define a portion of a sphere with center at the new head center. The computer calculates and stores the change in head center (from that calculated in step 154, above).

The physician will then return the femur to a natural reference position, "position 1" established in step 154 above. This position is achieved by moving the femur to a position in which the orientation of the femoral tracking marker approximately matches the orientation previously initialized (in step 156). The tracking system once again inputs the position of the femoral marker (step 212) and calculates the change in leg length and offset as compared with those initialized in step 156, above. Note that the absolute leg length and offset are at no time required. For successful surgical navigation it suffices to track and calculate the difference between the initial femoral tracker position (while the leg is in position 1) and the later tracker position (step 212, while leg is in position 1 again).

In general, steps 210 and 212 will calculate some change from initial head center, offset and leg length. This change may be insignificant, but if in the judgment of the surgeon it is significant (and undesirable) he may either (1) change the prosthetic head/neck to better approach a desired geometry, or (2) drive the implant stem deeper into the femur. The steps 210 and/or 212 would then be repeated until a desirable geometry is obtained. In many cases, the desired geometry may be a change from the pre-operative leg length and offset. The choice is within the discretion and control of the surgeon. This completes the "navigation" step (step 42 of FIG. 2).

Figure 12:
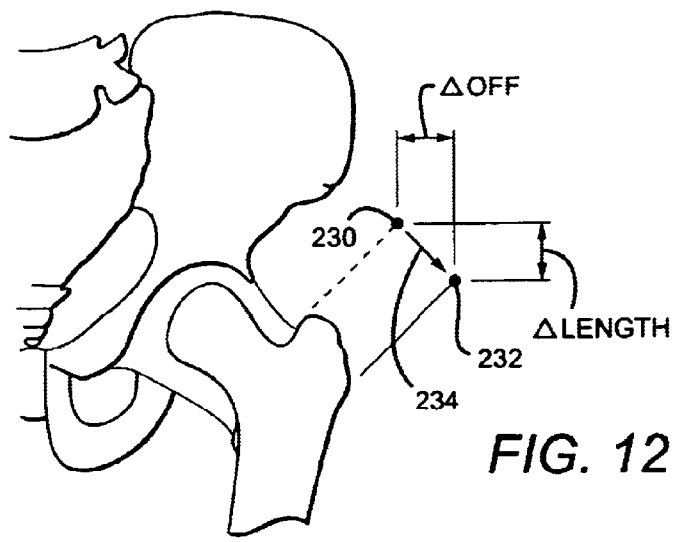
FIG. 12 is a frontal view of a hip joint, illustrating the geometry and defining a relative offset and leg length, as determined in the method of the invention.

FIG. 12 shows the geometry involved in the method of determining the change in both leg length and offset using optical tracking. Point 230 represents the position vector of an arbitrary point on the femoral tracker as tracked and acquired during acquisition step 154. Point 232 represents the position vector of the corresponding point of the femoral tracker, as sampled after the implantation in step 212. Small vector 234 represents the vector subtraction of the vector 232 from the vector 230. The vector subtraction is readily calculated, and it can be decomposed into components (projections) in any desired plane, by conventional vector geometry. The projection into the pelvic plane is convenient, but that into the central coronal plane could also be used.

Figure 13:
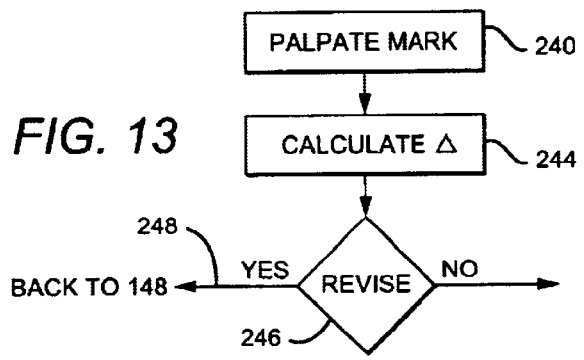
FIG. 13 is a flow diagram showing detailed steps suitable for executing the verification step of FIG. 2.

FIG. 13 shows details of the optional but highly preferred verification step (44 in FIG. 2). First, in synchrony with program execution, the physician uses the probe tip (52 FIG. 3) to touch the reference mark (pelvis) (cauterization or equivalent) which he previously made in step 152. The optical locator and computer calculate (step 244) the relationship between the reference mark and the fixed pelvic tracking marker (60 in FIG. 4). For example, the computer might calculate the position of the reference mark in the pelvic marker's reference frame (PTMRF). This position is compared with the previously calculated position of the marker in the same reference frame (from step 152) and the result is output for the physician's information. Based on the result, he/she may then either choose (step 246) to revise the procedure (via return path 248, because the check shows that something moved) or end the surgery (if the check shows insignificant movement). This procedure provides a redundant "tracker check" feature which reassures the physician that the tracking accuracy has not been compromised due to unintentional tracking marker movement.

Preferably, a similar tracker check procedure should be performed to check the fixation of the femoral tracking marker: during initialization the physician may make a reference mark on the femur, then after the implantation he can touch the mark and check for slippage by finding the coordinates of the reference mark in the reference frame of the femoral tracking marker 68.

Finally, it is highly desirable that the system records a permanent record of the procedure, or at least a summary suitable for inclusion into the patient's file. FIG. 14 shows a typical screen capture or printout which includes acetabular shell version and abduction (as measured by the impactor tool), shell angles, liner angles, head center change, leg length change, and leg offset change. It is also convenient to provide a machine readable record of the surgery, on a medium such as CD-R or its equivalent.

While several illustrative embodiments of the invention have been shown and described, numerous variations and alternate embodiments will occur to those skilled in the art. In some operations the acetabular implant might not be required, but the femoral navigation methods and apparatus of the invention are still applicable. The procedure may be repeated on both sides of the body in a bi-lateral THR operation. Different elastomeric straps, fibers, cords, mesh, wire, adhesives or ligatures could be employed in connection with the femoral tracking marker device. The fixed pelvic marker could also be fixed by alternate methods such as clamps, pins or even adhesives. The method can be adapted to various body geometries and sizes, and indeed could even be adapted, with small modifications, for veterinary medicine. Tracking means other than but equivalent to optical could be substituted, such as radio, microwave, magnetic, sonic or ultrasonic tracking systems, provided that the system be not so clumsy or bulky as to interfere with the surgical manipulations required. The geometries of the various tools and markers can be varied or modified to accommodate different tracking approaches. Active or passive optical targets can be used on the tracking markers. Such variations and alternate embodiments are contemplated, and can be made without departing from the spirit and scope of the invention as defined in the appended claims.

We claim:

1. A method of verifying reliability of a computer assisted, optically tracked surgical navigation system, comprising the steps of:

fixing an optically trackable marker to a bone at a point of attachment;

placing a mark on said bone at a location removed from said point of attachment;

inputting an initial position of said mark into an optical tracking system by touching said mark with an optically trackable probe, while simultaneously tracking said optically trackable marker;

calculating an initial vector locating said mark in the reference frame of said optically trackable marker;

at a later time, inputting a later position of said mark into the optical tracking system by touching said mark again with the optically trackable probe, while simultaneously tracking said optically trackable marker;

calculating a second vector locating the later position of said mark in the later reference frame of the optically trackable marker; and comparing said initial and said later vectors to verify that said optically trackable marker has remained fixed relative to said mark.

2. The method of claim 1, wherein said mark is made by cauterization.

3. The method of claim 1, wherein said optically trackable marker is fixed by a bone screw.

4. The method of claim 1, wherein said optically trackable marker is fixed by a collar and opposing ligature.

5. The method of claim 1, wherein said optically trackable marker is fixed by a clamp.

* * * * *